(12) United States Patent
Song et al.

(10) Patent No.: US 9,678,020 B2
(45) Date of Patent: Jun. 13, 2017

(54) APPARATUS AND METHOD FOR INSPECTION OF SUBSTRATE DEFECT

(71) Applicants: Joon-Seo Song, Seoul (KR); Woo-seok Ko, Seoul (KR); Ji-Young Shin, Suwon-si (KR); Seong-Jin Yun, Yongin-si (KR); Yu-Sin Yang, Seoul (KR); Sang-Kil Lee, Yongin-si (KR); Chung-Sam Jun, Suwon-si (KR)

(72) Inventors: Joon-Seo Song, Seoul (KR); Woo-seok Ko, Seoul (KR); Ji-Young Shin, Suwon-si (KR); Seong-Jin Yun, Yongin-si (KR); Yu-Sin Yang, Seoul (KR); Sang-Kil Lee, Yongin-si (KR); Chung-Sam Jun, Suwon-si (KR)

(73) Assignee: Samsung Electronics Co., Ltd., Geyonggi-do (KR)

( * ) Notice: Subject to any disclaimer, the term of this patent is extended or adjusted under 35 U.S.C. 154(b) by 11 days.

(21) Appl. No.: 14/795,396

(22) Filed: Jul. 9, 2015

(65) Prior Publication Data

US 2016/0025654 A1    Jan. 28, 2016

(30) Foreign Application Priority Data

Jul. 28, 2014 (KR) .................. 10-2014-0095832

(51) Int. Cl.
*G01N 21/95* (2006.01)
*G01N 21/88* (2006.01)
*G01N 21/956* (2006.01)

(52) U.S. Cl.
CPC ..... *G01N 21/9505* (2013.01); *G01N 21/8806* (2013.01); *G01N 21/9501* (2013.01); *G01N 21/95692* (2013.01); *G01N 2201/061* (2013.01)

(58) Field of Classification Search
CPC .......... G01N 21/8806; G01N 21/9501; G01N 2201/06113
See application file for complete search history.

(56) References Cited

U.S. PATENT DOCUMENTS

| | | |
|---|---|---|
| 6,232,787 B1 | 5/2001 | Lo et al. |
| 6,525,318 B1 | 2/2003 | Kim et al. |
| 6,545,491 B2 | 4/2003 | Kim et al. |
| 7,019,292 B1 | 3/2006 | Fan et al. |

(Continued)

FOREIGN PATENT DOCUMENTS

| | | | |
|---|---|---|---|
| KR | 2000-0012913 A | 3/2000 |
| KR | 2000-0067104 A | 11/2000 |

(Continued)

*Primary Examiner* — David Porta
*Assistant Examiner* — Faye Boosalis
(74) *Attorney, Agent, or Firm* — Harness, Dickey & Pierce, P.L.C.

(57) ABSTRACT

Example embodiments relate to an apparatus and method for inspecting a substrate defect. The substrate defect inspecting apparatus includes a substrate, a light source emitting an infrared beam to the substrate, a detector detecting the infrared beam reflected from the substrate, and a defect analyzer receiving first information and second information from the detector and analyzing defects existing in the substrate. According to at least one example embodiment, the second information is acquired during a later process than the first information.

17 Claims, 20 Drawing Sheets

(56) References Cited

U.S. PATENT DOCUMENTS

| | | |
|---|---|---|
| 8,134,699 B2 | 3/2012 | Naftali et al. |
| 8,139,844 B2 | 3/2012 | Chen et al. |
| 8,213,704 B2 | 7/2012 | Peterson et al. |
| 8,625,090 B2 | 1/2014 | Lee et al. |
| 8,675,188 B2 | 3/2014 | Liu et al. |
| 2002/0088952 A1* | 7/2002 | Rao .................. G01N 21/9501 |
| | | 250/559.45 |

FOREIGN PATENT DOCUMENTS

| | | |
|---|---|---|
| KR | 2001-0073412 A | 8/2001 |
| KR | 2002-0016314 A | 3/2002 |
| KR | 2006-0076067 A | 7/2006 |
| KR | 2012-0029887 A | 3/2012 |

\* cited by examiner

21

22

APPARATUS AND METHOD FOR INSPECTION OF SUBSTRATE DEFECT

CROSS-REFERENCE TO RELATED APPLICATION

This application claims priority from Korean Patent Application No. 10-2014-0095832 filed on Jul. 28, 2014 in the Korean Intellectual Property Office, and all the benefits accruing therefrom under 35 U.S.C. 119, the contents of which are herein incorporated by reference in their entirety.

BACKGROUND

1. Field of the Inventive Concept

Example embodiments relate to an apparatus and/or a method for inspecting a substrate defect.

2. Description of the Related Art

According to diversification of semiconductor processes and accelerated mass production of semiconductor products, in-line monitoring technology in which the presence or absence of defects of a semiconductor wafer is inspected immediately after each process step is completed has become more and more prevalent. Nowadays, vertical type semiconductor products are predominantly being produced due to limitations in the design rule of planar type semiconductor products. Accordingly, it may be advantageous to propose technology for monitoring defects or contact failures of vertical type semiconductor products in real time.

SUMMARY

Example embodiments relate to a substrate defect inspecting apparatus that can inspect defects existing at a lower portion of a contact hole using light having a wavelength in an infrared region. In particular, the defects existing at the lower portion of the contact hole may be inspected by an in-line monitoring method based on skew defect analysis (SDA).

Example embodiments relate to a substrate defect inspecting method that can inspect defects existing at a lower portion of a contact hole using light having a wavelength in an infrared region.

These and other objects of the example embodiments will be described in or be apparent from the following description.

Example embodiments relate to a substrate defect inspecting apparatus that includes a substrate, a light source emitting an infrared beam to the substrate, a detector detecting the infrared beam reflected from the substrate, and a defect analyzer receiving first information and second information from the detector and analyzing defects existing in the substrate, wherein the second information is acquired in a later process than the first information.

Example embodiments relate to a substrate defect inspecting apparatus including a substrate, a light source emitting an infrared beam to the substrate, a detector detecting the infrared beam reflected from the substrate, an image processor converting an analog signal received from the detector into a digital image, and a defect analyzer creating first and second defect images based on the digital image, comparing the first and second defect images with each other, and analyzing a defect existing in the substrate.

Example embodiments relate to a substrate defect inspecting apparatus including a light source emitting light having a wavelength ranging from substantially 600 nm to substantially 900 nm, a contact hole bottom surface configured to receive and reflect light, and a detector detecting the light reflected from the contact hole bottom surface, wherein defects existing in the contact hole bottom surface using information concerning the light are detected by the detector.

Example embodiments relate to a substrate defect inspecting method including emitting a first infrared beam toward a substrate, detecting a second infrared beam reflected from the substrate, forming contact holes in the substrate, emitting a third infrared beam toward the contact holes, detecting a fourth infrared beam reflected from bottom surfaces of the contact holes, and detecting defects existing on the bottom surfaces of the contact holes using the second and fourth infrared beams.

Example embodiments relate to a defect analyzing apparatus including a substrate, a light source configured to emit a radiation beam on the substrate, a detector configured to detect a first reflected beam from the substrate corresponding to a first state of the substrate and a second reflected beam from the substrate corresponding to a second state of the substrate, and a defect analyzer configured to analyze defects in the substrate based on the detected first reflected beam and the detected second reflected beam.

BRIEF DESCRIPTION OF THE DRAWINGS

The above and other features and advantages of the example embodiments will become more apparent with reference to the attached drawings in which.

DETAILED DESCRIPTION OF THE EMBODIMENTS

Figure 1:
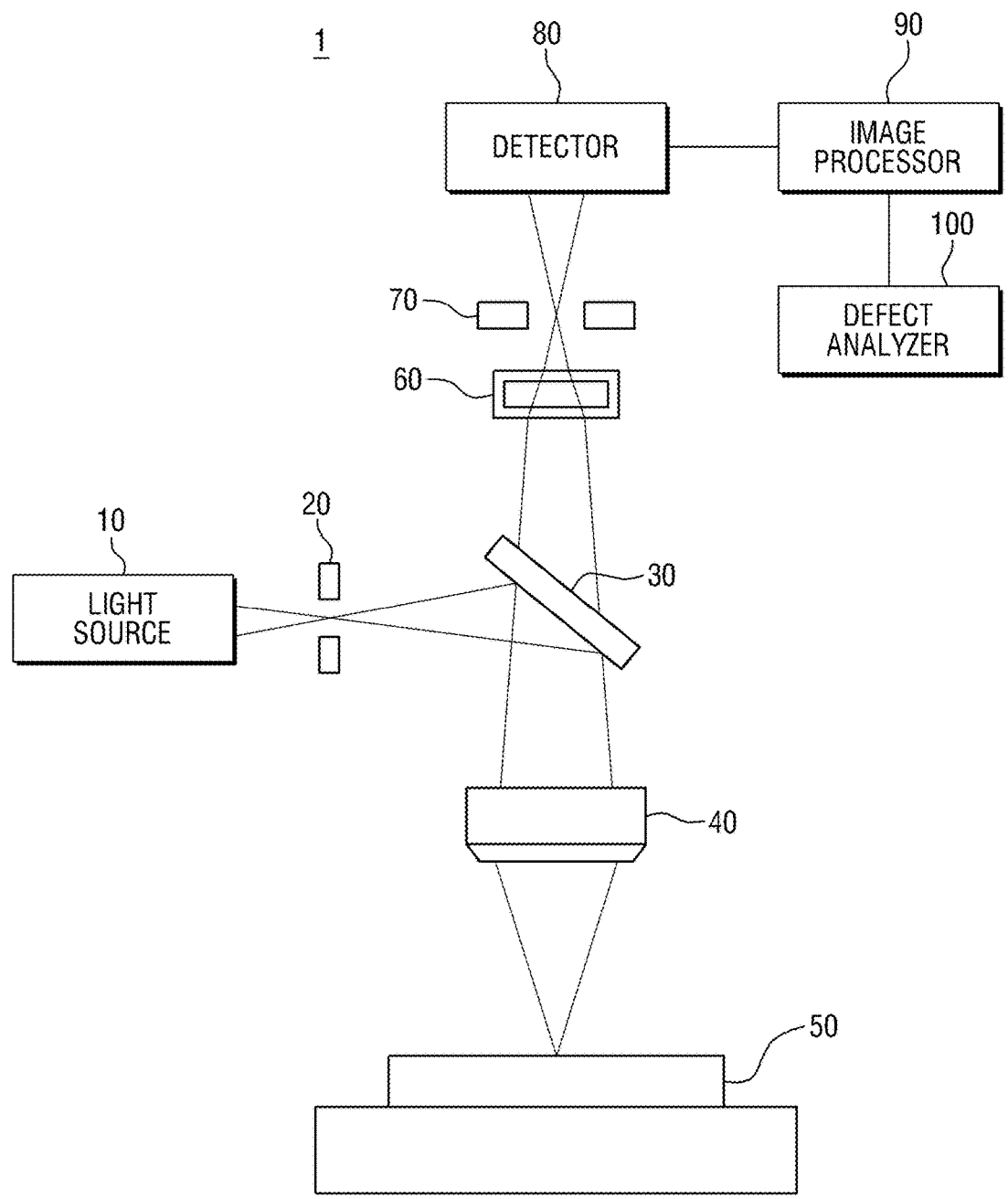
FIG. 1 is a schematic diagram illustrating a substrate defect inspecting apparatus according to a first example embodiment.

Example embodiments will now be described more fully hereinafter with reference to the accompanying drawings. This example embodiments may, however, be embodied in different forms and should not be construed as limited to the embodiments set forth herein. Rather, these example embodiments are provided so that this disclosure will be thorough and complete, and will fully convey the scope of the example embodiments to those skilled in the art. The same reference numbers indicate the same components throughout the specification. In the attached figures, the thickness of layers and regions is exaggerated for clarity.

It will be understood that when an element is referred to as being "on," "connected" or "coupled" to another element, it can be directly on, connected or coupled to the other element or intervening elements may be present. In contrast, when an element is referred to as being "directly on," "directly connected" or "directly coupled" to another element, there are no intervening elements present. As used herein the term "and/or" includes any and all combinations of one or more of the associated listed items. Further, it will be understood that when a layer is referred to as being "under" another layer, it can be directly under or one or more intervening layers may also be present. In addition, it will also be understood that when a layer is referred to as being "between" two layers, it can be the only layer between the two layers, or one or more intervening layers may also be present.

It will be understood that, although the terms "first", "second", etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of example embodiments.

In the drawing figures, the dimensions of layers and regions may be exaggerated for clarity of illustration. Like reference numerals refer to like elements throughout. The same reference numbers indicate the same components throughout the specification.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of example embodiments. The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (e.g., meaning "including, but not limited to,") unless otherwise noted.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of example embodiments.

Unless defined otherwise, all technical and scientific terms used herein have the same meaning as commonly understood by one of ordinary skill in the art to which this invention belongs. It is noted that the use of any and all examples, or exemplary terms provided herein is intended merely to better illuminate the invention and is not a limitation on the scope of the invention unless otherwise specified. Further, unless defined otherwise, all terms defined in generally used dictionaries may not be overly interpreted.

Although corresponding plan views and/or perspective views of some cross-sectional view(s) may not be shown, the cross-sectional view(s) of device structures illustrated herein provide support for a plurality of device structures that extend along two different directions as would be illustrated in a plan view, and/or in three different directions as would be illustrated in a perspective view. The two different directions may or may not be orthogonal to each other. The three different directions may include a third direction that may be orthogonal to the two different directions. The plurality of device structures may be integrated in a same electronic device. For example, when a device structure (e.g., a memory cell structure or a transistor structure) is illustrated in a cross-sectional view, an electronic device may include a plurality of the device structures (e.g., memory cell structures or transistor structures), as would be illustrated by a plan view of the electronic device. The plurality of device structures may be arranged in an array and/or in a two-dimensional pattern.

The example embodiments will be described with reference to perspective views, cross-sectional views, and/or plan views, in which example embodiments are shown. Thus, the profile of an exemplary view may be modified according to manufacturing techniques and/or allowances. That is, the example embodiments are not intended to limit the scope of the embodiments but cover all changes and modifications that can be caused due to a change in manufacturing process.

Thus, regions shown in the drawings are illustrated in schematic form and the shapes of the regions are presented simply by way of illustration and not as a limitation.

Figure 2:
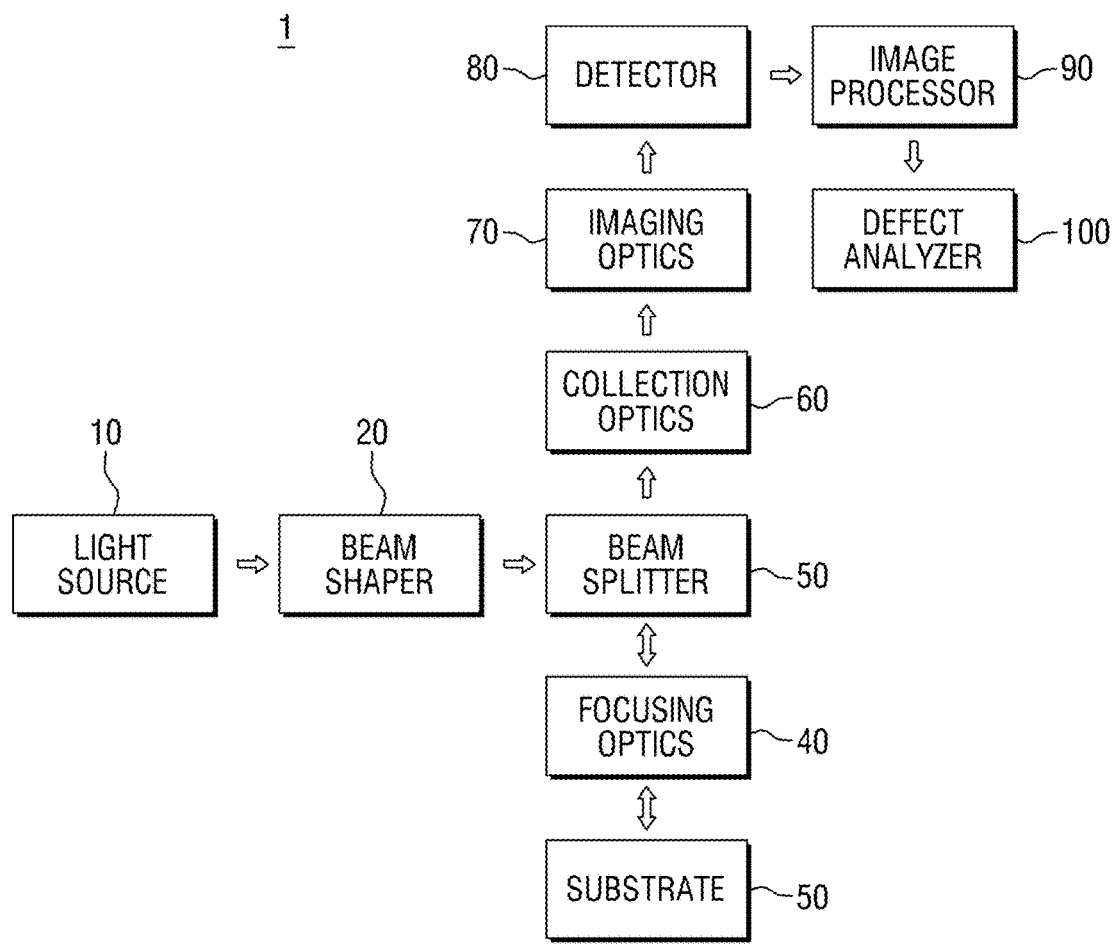
FIG. 2 is a block diagram of the substrate defect inspecting apparatus shown in FIG. 1.
Figure 3:
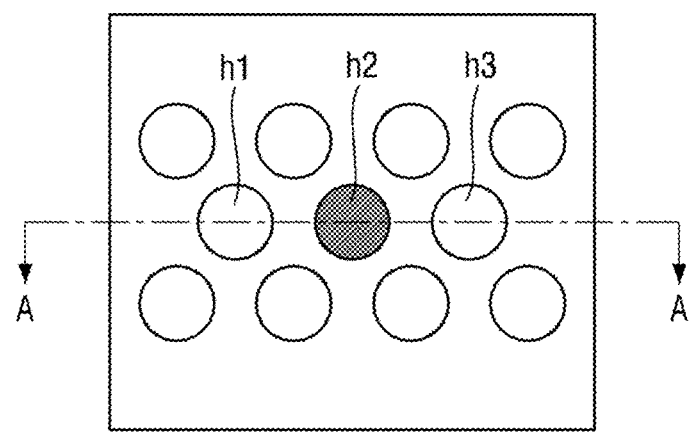
FIG. 3 illustrates a contact hole formed on a substrate, according to at least one example embodiment.
Figure 4:
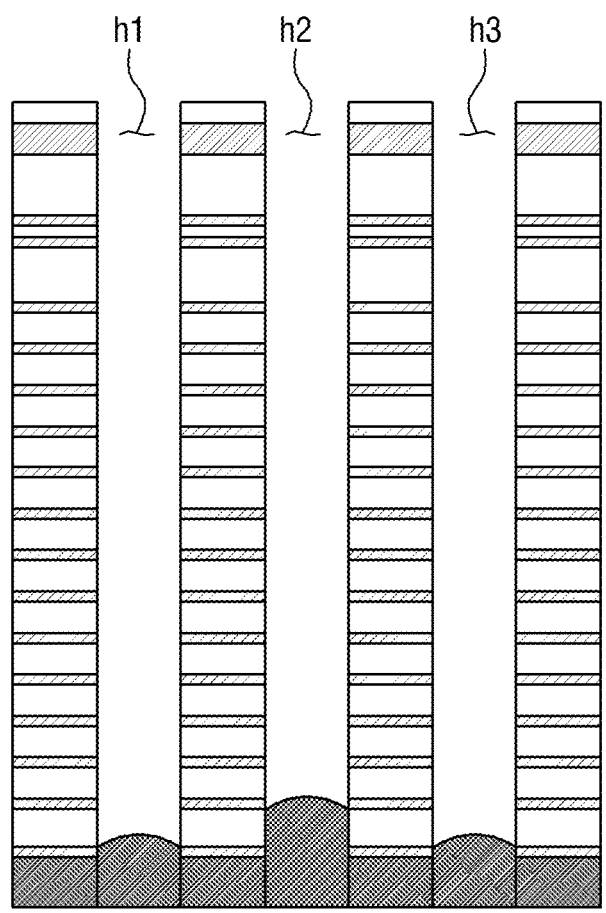
FIG. 4 is a cross-sectional view taken along the line A-A of FIG. 3.
Figure 5:
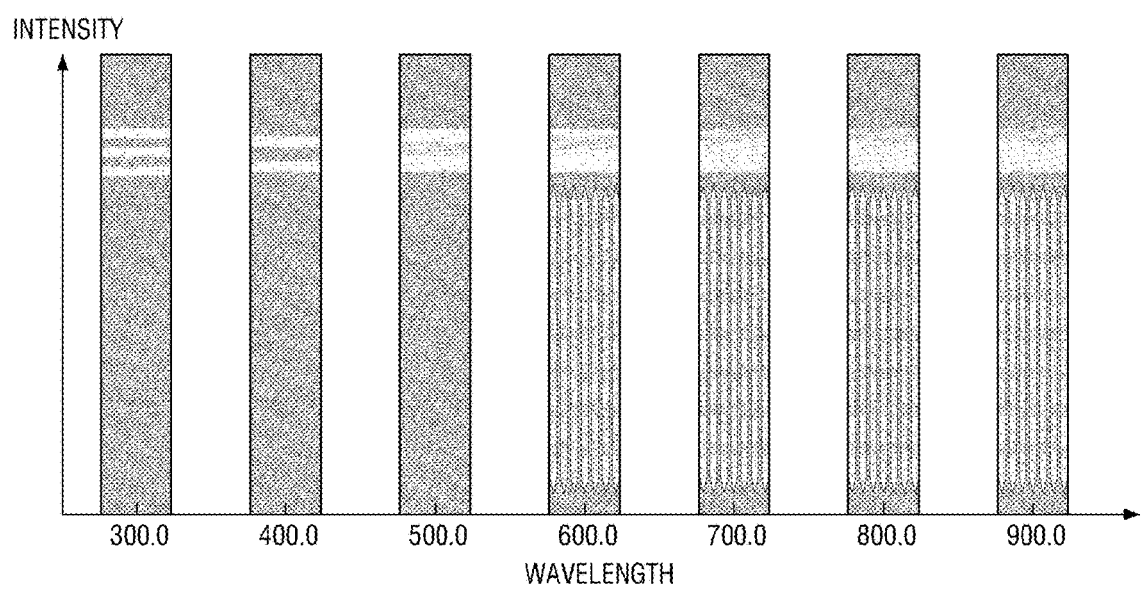
FIG. 5 is a graph illustrating the degree of light passing through a contact hole depending on the wavelength, according to at least one example embodiment.
Figure 6:
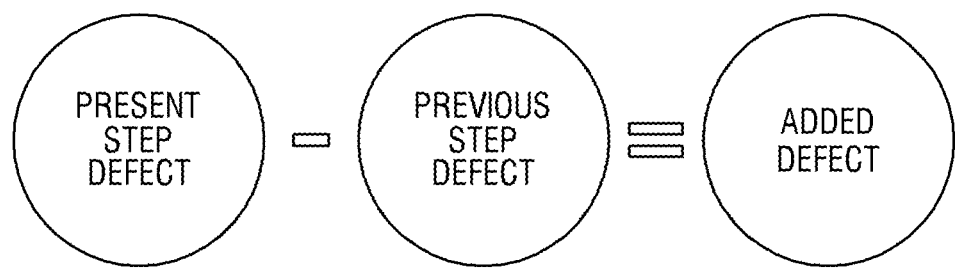
FIG. 6 is a diagram for explaining skew defect analysis (SDA)

FIG. 1 is a schematic diagram illustrating a substrate defect inspecting apparatus according to at least one example embodiment, FIG. 2 is a block diagram of the substrate defect inspecting apparatus shown in FIG. 1, FIG. 3 illustrates a contact hole formed on a substrate, FIG. 4 is a cross-sectional view taken along the line A-A of FIG. 3, FIG. 5 is a graph illustrating the degree of light passing through a contact hole depending on the wavelength, and FIG. 6 is a diagram for explaining skew defect analysis (SDA).

Referring to FIGS. 1 and 2, the substrate defect inspecting apparatus 1 according to at least one example embodiment includes a light source 10, a beam shaper 20, a beam splitter 30, a focusing optical system (focusing optics) 40, a substrate 50, a collection optics (collection optics) 60, an imaging optics (imaging optics) 70, a detector 80, an image processor 90, and a defect analyzer 100. According to at least one example embodiment, the detector 80, the image processor 90 and/or the defect analyzer 100 form a defect detecting architecture.

According to at least one example embodiment, the light source 10 emits an infrared beam having a wavelength in an infrared region (to be briefly referred to as an IR_beam, hereinafter) to the substrate 50. That is to say, the IR_beam emitted from the light source 10 reaches the substrate 50 through the beam shaper 20, the beam splitter 30 and the focusing optics 40.

Here, the light source 10 may emit the IR_beam, which has a wavelength ranging from about 600 nm to about 900 nm. Any kind of light source may be used as the light source 10, so long as the light source emits the IR_beam. The light source 10 emitting the IR_beam may be, for example, a laser diode (LD) or a light emitting diode (LED), but example embodiments are not limited thereto. The output power of the IR_beam may be adjusted.

According to at least one example embodiment, a light source emitting an IR_beam having a wavelength ranging from about 600 nm to about 900 nm is used as the light source 10. Referring to FIGS. 3 and 4, first to third contact holes h1, h2 and h3 formed in the substrate 50 are illustrated. Here, it is assumed that an overgrowth defect is generated in the second contact hole h2.

After a plurality of contact holes, including the first to third contact holes h1, h2 and h3, are formed in the substrate 50, in-line monitoring is performed to detect defects formed on bottom surfaces of the contact holes. When an IR_beam is supplied to the plurality of contact holes as targets, it is possible to monitor whether or not defects are generated in the plurality of contact holes by detecting a signal depending on the intensity of the IR_beam reflected from the bottom surfaces of the plurality of contact holes.

Referring to FIG. 5, when the IR_beam has a wavelength ranging from about 600 nm to about 900 nm, the light may reach the bottom surfaces of the contact holes. That is to say, the IR_beam having a wavelength ranging from about 300 nm to about 500 nm has a penetration depth at which the IR_beam can pass through only upper layers of the contact holes. However, when the IR_beam, having a wavelength ranging from about 600 nm to about 900 nm, has a penetration depth greater than the IR_beam having a wavelength ranging from about 300 nm to about 500 nm, the IR_beam may reach the bottom surfaces of the contact holes.

Therefore, when the IR_beam has a wavelength ranging from the IR_beam 600 nm to the IR_beam 900 nm is used, the presence or absence of defects in the bottom surfaces of the plurality of contact holes may be inspected through optical signal analysis using the light reflected from the bottom surfaces of the plurality of contact holes.

In addition, as a stacked structure is formed by processing step, a defect inspecting process of the previous step preceding the present or current step (e.g., a contact hole forming process) is performed, a defect inspecting process of the present or current step is performed, and both defect inspecting processes are compared to each other, thereby detecting an added defect that has been newly generated during the present or current step.

Referring to FIG. 6, SDA analysis is illustrated. As illustrated in FIG. 6, only the added defect newly generated in the present step can be detected by subtracting a digital image of the previous step defect from a digital image of the present step.

According to at least one example embodiment, the beam shaper 20 receives the IR_beam emitted from the light source 10 and transforms a state of the IR_beam. Here, the beam shaper 20 may be an aperture, a polarizer or a homogenizer.

Various types of apertures may be used as the beam shaper 20. The IR_beam may be transformed to have various shapes according to the aperture type. The aperture refers to an open part through which electrons, beams, electromagnetic waves or the like are radiated. When various types of apertures are used as the beam shaper 20, the intensity of the IR_beam reaching the substrate 50 may vary. Therefore, it may be advantageous to use an aperture having optimal conditions. The aperture will be described in greater detail below.

Alternatively, various types of polarizers may be used as the beam shaper 20. The polarizer refers to a device for obtaining linearly polarized light using the property of an optical isomer having changed colors of transmitted light of polarization according to the direction of polarization. The polarizer, including a rotating part, may adjust the direction of polarization of the IR_beam using the polarizer while rotating at various angles. Since the intensity of the IR_beam reaching the substrate 50 may vary according to the direction of polarization, it may be advantageous to adjust the direction of polarization so as to provide the optimal conditions.

Further, various types of homogenizers may be used as the beam shaper 20. The homogenizer produces flat light from the transmitted IR_beam. That is to say, a collimated IR_beam is converted into a flat-top beam having a spatially uniform energy distribution by the homogenizer to then be emitted in parallel. When various types of homogenizers are used as the beam shaper 20, the intensity of the IR_beam reaching the substrate 50 may vary. Therefore, it may be advantageous to use a homogenizer providing the optimal conditions.

According to at least one example embodiment, the beam splitter 30 may receive and reflect the IR_beam having passed through the beam shaper 20 or may allow the IR_beam reflected from the substrate 50 to pass through the beam splitter 30. A beam splitter may refer to an optical device, such as a reflecting mirror, a diffraction lattice, a Fresnel zone plate, a diffusion plate, or the like, reflecting some of the beams while allowing the other beams to pass therethrough. Because the beam splitter 30 is an optical device that splits incident light ray fluxes into two groups, the beam splitter 30 may receive the IR_beam having passed through the beam shaper 20 to allow the received IR_beam to be reflected to the substrate 50 while allowing the IR_beam reflected from the substrate 50 to pass through the beam splitter 30.

According to at least one example embodiment, the focusing optics 40 focuses the IR_beam reflected from the beam splitter 30 to the substrate 50. The focusing optics 40 may provide the IR_beam focused onto the substrate 50 to increase the intensity of light reaching the substrate 50. As sizes of contact holes formed in the substrate 50 are reduced, the light may not reach the bottom surfaces of the contact holes unless the light reaching the substrate 50 is concentrated by an apparatus for inspecting defects existing in the contact holes. In at least one example embodiment, the IR_beam having a relatively large penetration depth is used. However, in order to increase the amount of light reaching the substrate 50, the focusing optics 40 are preferably used.

According to at least one example embodiment, the substrate 50 may be a semiconductor substrate. The substrate 50 may include, silicon (Si), strained Si, a silicon alloy, silicon carbide (SiC), silicon germanium (SiGe), silicon germanium carbide (SiGeC), germanium, a germanium alloy, gallium arsenide (GaAs), indium arsenide (InAs), one of III-V group semiconductor compounds, one of II-VI group semiconductor compounds, and stacks or combinations thereof. In addition, the substrate 50 may be an organic plastic substrate, rather than a semiconductor substrate.

In at least one example embodiment, it is assumed that contact holes are formed in the substrate 50. That is to say, the at least one example embodiment is directed to a defect inspecting apparatus for inspecting defects existing on bottom surfaces of contact holes, which are formed in a stacked structure. Thus, various kinds of substrates used in fabricating semiconductor products may be used as the substrate 50.

According to at least one example embodiment, the collecting optics 60 focuses the IR_beam having passed through the beam splitter 30. That is to say, the IR_beam reflected from the substrate 50 passes through the beam splitter 30, and the collecting optics 60 focuses IR_beam having passed through the beam splitter 30 to obtain various pieces of information from the focused IR_beam.

Before the formation of contact holes in the substrate 50, a substrate inspecting process may be performed to obtain information concerning a state of the substrate 50 from the IR_beam reflected from the substrate 50. Then, after the formation of the contact holes in the substrate 50, a substrate inspecting process may be performed to obtain information concerning states of bottom surfaces of the contact holes from the IR_beam reflected from the bottom surfaces of the contact holes. During the aforementioned procedure, the collecting optics 60 serves to increase a possibility of easily obtaining the information by focusing the IR_beam to allow the focused IR_beam to reach the detector 80.

If the IR_beam is focused by the collecting optics 60, the amount of light reaching the detector 80 may increase, and the information concerning the IR_beam reflected from the substrate 50 or the bottom surfaces of the contact holes can be more easily obtained as a result.

The imaging optics 70 transforms the state of the IR_beam having passed through the collecting optics 60 or changes a magnification of the collecting optics 60. That is to say, the imaging optics 70 may also be an aperture, a polarizer or a homogenizer.

When the imaging optics 70 includes various types of apertures, the IR_beam having passed through the collecting optics 60 may be transformed to have various shapes according to the aperture type. Since the intensity of the IR_beam reaching the detector 80 may vary, it may be advantageous to use an aperture having optimal conditions.

Alternatively, the imaging optics 70 may include various types of polarizers. When the imaging optics 70 includes various types of polarizers, the direction of polarization of the IR_beam having passed through the collecting optics 60 may be adjustable. Since the intensity of the IR_beam reaching the detector 80 may vary according to the direction of polarization, it may be advantageous to adjust the direction of polarization so as to provide optimal conditions.

Further, the imaging optics 70 may include various types of homogenizers. When the imaging optics 70 includes various types of homogenizers, the intensity of the IR_beam reaching the detector 80 may vary. Therefore, it may be advantageous to use a homogenizer providing the optimal conditions.

According to at least one example embodiment, the detector 80 detects the IR_beam reflected from the substrate 50 and having passed through the focusing optics 40, the beam splitter 30, the collecting optics 60 and the imaging optics 70. A state of the substrate 50 or states of the bottom surfaces of the contact holes may be identified using the IR_beam detected by the detector 80. For example, when the information concerning a defect existing in the substrate 50 is known and the information concerning defects existing on the bottom surfaces of the contact holes is known, it is possible to obtain information concerning defects generated during the contact hole forming process.

The defects existing on the bottom surfaces of the contact holes may be overgrowth defects or missing defects. When the overgrowth defects or missing defects are produced on the bottom surfaces of the contact holes, the IR_beam having different amounts of light is reflected, and the intensity of the IR_beam detected by the detector 80 may vary. If such differences are previously known, information concerning defects may be collected into a database, to thereby facilitate rapidly performing a defect inspecting process.

The image processor 90 converts an analog signal received from the detector 80 into a digital image. The image processor 90 generates the digital image using the information concerning the intensity of the IR_beam detected by the detector 80. A digitized defect image is overlapped with the image of the substrate 50, thereby allowing a user to easily identify a defect existing in the substrate 50.

According to at least one example embodiment, the defect analyzer 100 generates a first defect image and a second defect image based on the digital image provided from the image processor 90, compares the first defect image with the second defect image, and analyzes defects existing on the bottom surfaces of the contact holes.

The defect analyzer 100 may analyze the defects existing on the bottom surfaces of the contact holes, which are generated in the contact hole forming process, using a digital image i1 concerning the defect existing in the substrate 50 and a digital image i2 concerning the defects existing on the bottom surfaces of the contact holes.

When the digital image i1 is subtracted from the digital image i2, only a digital image i3 concerning defects generated in the contact hole forming process may be obtained, thereby easily identifying the defects existing on the bottom surfaces of the contact holes.

According to at least one example embodiment, when overgrowth defects are produced on the bottom surfaces of the contact holes, bright portions may appear on the digital image i3, and when missing defects are produced on the bottom surfaces of the contact holes, dark portions may appear on the digital image i3.

The defect analyzer 100 may perform contact hole inspection based on desired, or alternatively predetermined coordinate information on the substrate 50. That is to say, coordinates of the substrate 50 may be generated and contact holes may be formed at locations corresponding to the coordinates. The locations at which contact holes are formed may be identified using the desired, or alternatively predetermined coordinate information by repeating the contact hole forming processes, and the defects existing on the bottom surfaces of the contact holes can be inspected by emitting IR_beam to the locations in the above-described manner.

Figure 7:
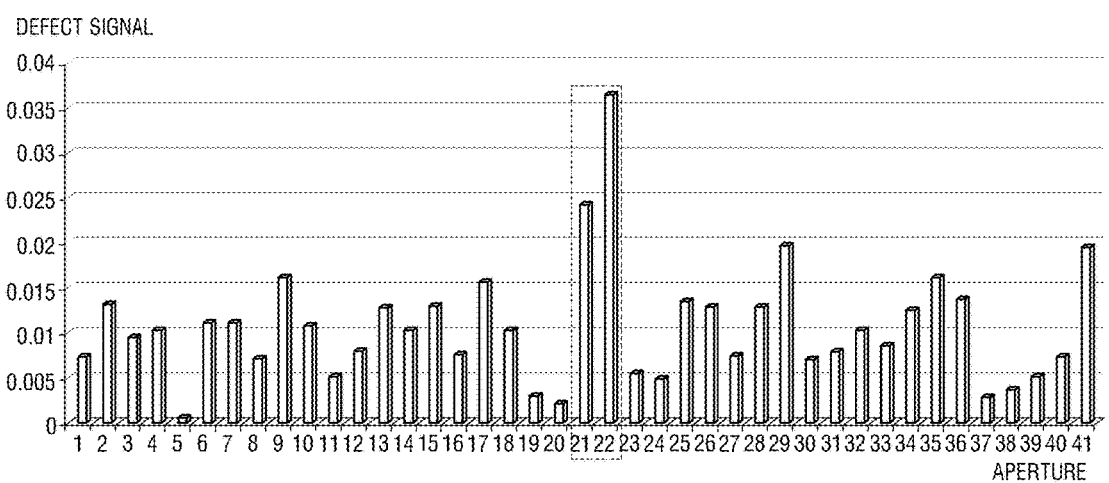
FIG. 7 is a graph illustrating the intensity of a signal generated from a defect according to the aperture type.
Figure 8:
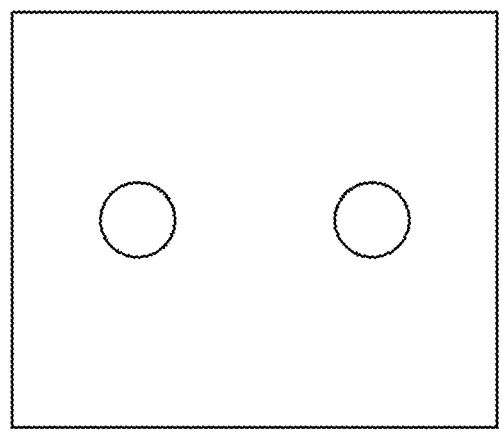
FIGS. 8 and 9 illustrate types of apertures having relatively high intensity of signals generated from defects, according to at least one example embodiment.
Figure 9:
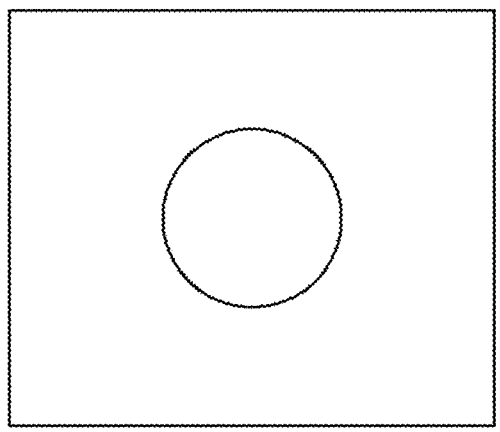

Specifically, FIG. 7 illustrates the signal intensity of the IR_beam reflected from the defects existing on the bottom surfaces of the contact holes according to the aperture type when using an aperture as the beam shaper 20. In FIG. 7, aperture No. 21 and aperture No. 22 are illustrated in FIGS. 8 and 9, and a relatively high signal intensity can be obtained based on the aperture type. In particular, when the aperture has a numerical aperture (NA) of approximately 0.5, relatively high signal intensity can be obtained.

Figure 10:
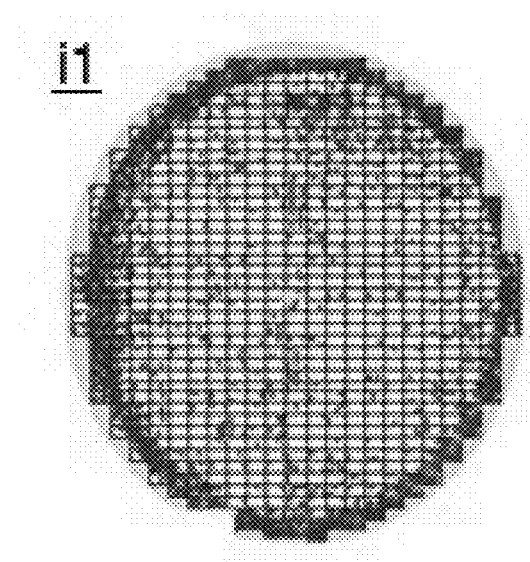
FIGS. 10 to 12 illustrate a process of analyzing a defect using SDA, according to at least one example embodiment.
Figure 11:
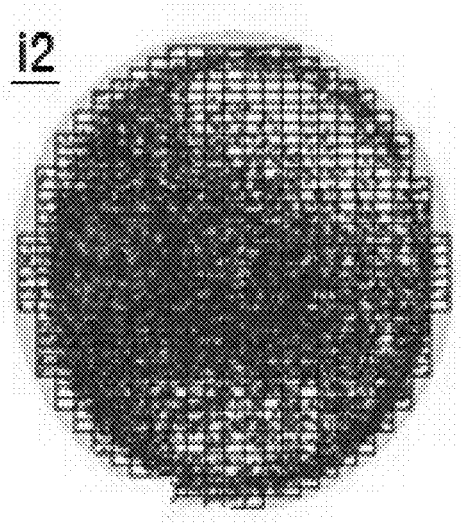
Figure 12:
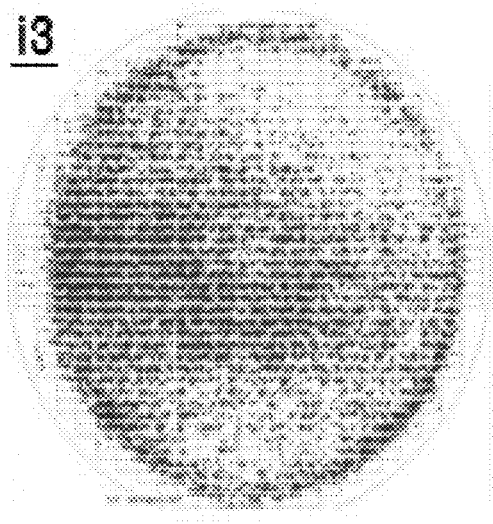

Referring to FIGS. 10 to 12, an example defect analysis using SDA is illustrated. FIGS. 10 to 12 illustrate digital images generated by the image processor 90. Specifically, FIG. 10 illustrates a digital image i1 concerning a defect existing in the substrate 50, FIG. 11 illustrates a digital image i2 concerning defects existing on the bottom surfaces of the contact holes, and FIG. 12 illustrates a digital image i3 concerning defects generated in the contact hole forming process.

According to at least one example embodiment, FIG. 11 illustrates a digital image generated by performing a defect inspection process after the contact hole forming process. Since the image concerning defects generated in the contact hole forming process is included in the image concerning a defect previously existing on the substrate 50, a difference between the digital image i2 and the digital image i1 may correspond to the digital image i3 concerning the defects generated during the contact hole forming process.

Hereinafter, a substrate defect inspecting apparatus according to at least one example embodiment will be described.

Figure 13:
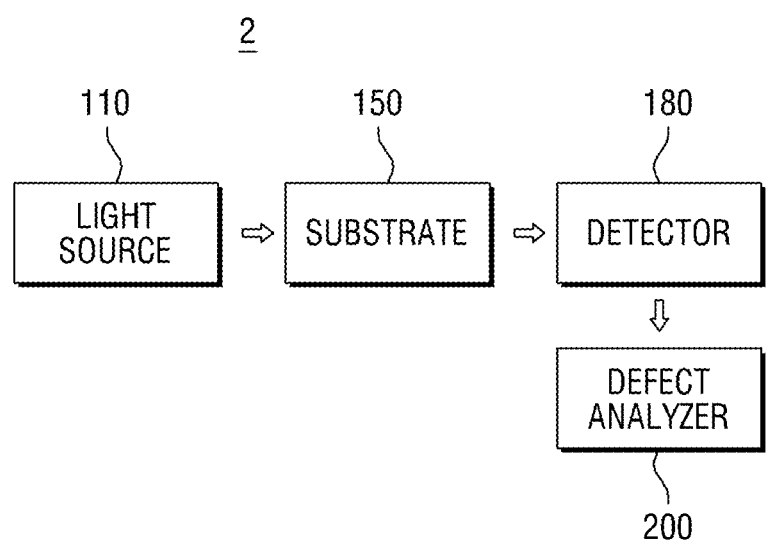
FIG. 13 is a block diagram of a substrate defect inspecting apparatus according to at least one example embodiment.

FIG. 13 is a block diagram of a substrate defect inspecting apparatus according to at least one example embodiment. For brevity, substantially the same portions of the substrate defect inspecting apparatus according to this example embodiment as those of the substrate defect inspecting apparatus according to the above example embodiment will not be repeated.

Referring to FIG. 13, the substrate defect inspecting apparatus 2 according to at least one example embodiment includes a light source 110, a substrate 150, a detector 180 and a defect analyzer 200.

The light source 110 emits an IR_beam to the substrate 150. Here, the light source 110 may emit an IR_beam having a wavelength ranging from about 600 nm to about 900 nm.

The light source 110 emitting the IR_beam may be, for example, a laser diode LD or a light emitting diode (LED), but example embodiments are not limited thereto. The output power of the IR_beam emitted from the light source 110 may be adjusted.

The substrate 150 may be a semiconductor substrate. The substrate 150 may include, silicon (Si), strained Si, a silicon alloy, silicon carbide (SiC), silicon germanium (SiGe), silicon germanium carbide (SiGeC), germanium, a germanium alloy, gallium arsenide (GaAs), indium arsenide (InAs), one of III-V group semiconductor compounds, one of II-VI group semiconductor compounds, and stacks thereof. In addition, the substrate 150 may be an organic plastic substrate, rather than a semiconductor substrate.

The substrate defect inspecting apparatus 2 may be configured to inspect defects existing on bottom surfaces of contact holes formed in a stacked structure provided on the substrate 150.

According to at least one example embodiment, the detector 180 detects the IR_beam reflected from the substrate 150. A state of the substrate 150 or states of the bottom surfaces of the contact holes may be identified using the IR_beam detected by the detector 180. For example, when the information concerning a defect existing in the substrate 150 is known and the information concerning defects existing on the bottom surfaces of the contact holes is known, it is possible to obtain information concerning defects generated during a contact hole forming process.

The defects existing on the bottom surfaces of the contact holes may be overgrowth defects or missing defects. When the overgrowth defects or missing defects are produced on the bottom surfaces of the contact holes, the IR_beam having different amounts of light is reflected, and the intensity of the IR_beam detected by the detector 180 may vary.

The defect analyzer 200 receives first information if1 and second information if2 from the detector 180 and analyzes the defects existing on the bottom surfaces of the contact holes.

According to at least one example embodiment, the second information if2 may be information acquired in a later process than the first information if1. That is to say, the first information if1 may be information concerning a defect existing in the substrate 150 prior to the contact hole forming process, and the second information if2 may be information concerning defects existing on the bottom surfaces of the contact holes after the contact hole forming process.

The defect analyzer 200 may perform contact hole inspection based on desired, or alternatively predetermined coordinate information on the substrate 150. That is to say, coordinates of the substrate 150 may be generated and contact holes may be formed at locations corresponding to the coordinates. The locations at which contact holes are formed may be identified using the desired, or alternatively predetermined coordinate information by repeating the contact hole forming processes, and the defects existing on the bottom surfaces of the contact holes can be inspected by emitting IR_beam to the locations in the above-described manner.

Figure 14:
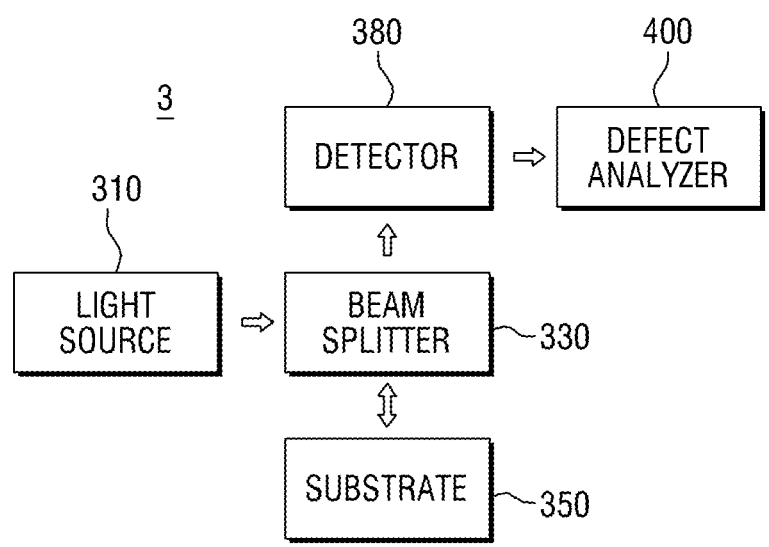
FIG. 14 is a block diagram of a substrate defect inspecting apparatus according to at least one example embodiment.

FIG. 14 is a block diagram of a substrate defect inspecting apparatus according to at least one example embodiment. For brevity, substantially the same portions of the substrate defect inspecting apparatus according to this example embodiment as those of the substrate defect inspecting apparatus according to the above example embodiment will not be repeated.

Referring to FIG. 14, the substrate defect inspecting apparatus 3 apparatus according to at least one example embodiment includes a light source 310, a beam splitter 330, a substrate 350, a detector 380, and a defect analyzer 400.

The light source 310 emits an IR_beam to the beam splitter 330. Here, the light source 310 may emit the IR_beam, which has a wavelength ranging from about 600 nm to about 900 nm.

The light source 310 emitting the IR_beam may be, for example, a laser diode LD or a light emitting diode (LED), but example embodiments are not limited thereto. The output power of the IR_beam emitted from the light source 310 may be adjusted.

The beam splitter 330 is configured to receive and reflect the IR_beam received from the light source 310 or to allow the IR_beam reflected from the substrate 350 to pass therethrough.

The substrate 350 may be a semiconductor substrate. The substrate 350 may include, silicon (Si), strained Si, a silicon alloy, silicon carbide (SiC), silicon germanium (SiGe), silicon germanium carbide (SiGeC), germanium, a germanium alloy, gallium arsenide (GaAs), indium arsenide (InAs), one of III-V group semiconductor compounds, one of II-VI group semiconductor compounds, and stacks thereof. In addition, the substrate 350 may be an organic plastic substrate, rather than a semiconductor substrate.

The substrate defect inspecting apparatus 3 may be configured to inspect defects existing on bottom surfaces of contact holes formed in a stacked structure provided on the substrate 350.

According to at least one example embodiment, the detector 380 detects the IR_beam reflected from the substrate 350 and having through the beam splitter 330. A state of the substrate 350 or states of the bottom surfaces of the contact holes may be identified using the IR_beam detected by the detector 380. For example, when the information concerning a defect existing in the substrate 350 is known and the information concerning defects existing on the bottom surfaces of the contact holes is known, it is possible to obtain information concerning defects generated during a contact hole forming process.

The defects existing on the bottom surfaces of the contact holes may be overgrowth defects or missing defects. When the overgrowth defects or missing defects are produced on the bottom surfaces of the contact holes, the IR_beam having different amounts of light is reflected, and the intensity of the IR_beam detected by the detector 380 may vary.

The defect analyzer 400 may receive third information if3 and fourth information if4 from the detector 380 and analyzes defects existing on the bottom surfaces of the contact holes.

According to at least one example embodiment, the fourth information if4 may be information acquired in a later process than the third information if3. That is to say, the third information if3 is information concerning a defect existing in the substrate 350 prior to the contact hole forming process, and the fourth information if4 is information concerning defects existing on the bottom surfaces of the contact holes after the contact hole forming process.

The defect analyzer 400 may be configured to perform contact hole inspection based on desired, or alternatively predetermined coordinate information on the substrate 350. That is to say, coordinates of the substrate 350 may be generated and contact holes may be formed at locations corresponding to the coordinates. The locations at which contact holes are formed may be identified using the desired, or alternatively predetermined coordinate information by repeating the contact hole forming processes, and the defects existing on the bottom surfaces of the contact holes can be inspected by emitting IR_beam to the locations in the above-described manner.

Figure 15:
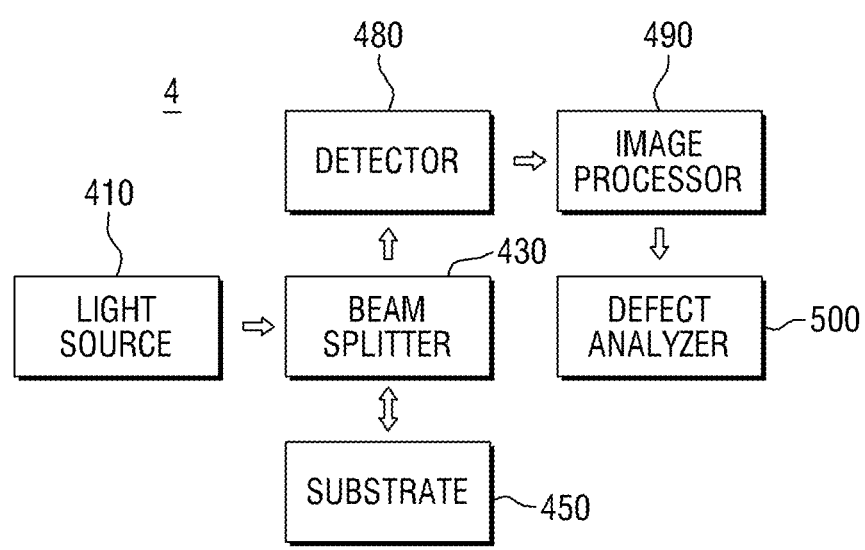
FIG. 15 is a block diagram of a substrate defect inspecting apparatus according to at least one example embodiment.

FIG. 15 is a block diagram of a substrate defect inspecting apparatus according to at least one example embodiment. For brevity, substantially the same portions of the substrate defect inspecting apparatus according to the current example embodiment as those of the substrate defect inspecting apparatus according to the above example embodiment will not be repeated.

Referring to FIG. 15, the substrate defect inspecting apparatus 4 according to the example embodiment includes a light source 410, a beam splitter 430, a substrate 450, a detector 480, an image processor 490, and a defect analyzer 500.

The light source 410 emits an IR_beam to the beam splitter 430. Here, the light source 410 may emit the IR_beam having a wavelength ranging from about 600 nm to about 900 nm.

The light source 410 emitting the IR_beam may be, for example, a laser diode LD or a light emitting diode (LED), but example embodiments are not limited thereto. The output power of the IR_beam emitted from the light source 410 may be adjusted.

The beam splitter 430 is configured to receive and reflect the IR_beam received from the light source 410 or to allow the IR_beam reflected from the substrate 450 to pass therethrough.

The substrate 450 may be a semiconductor substrate. The substrate 450 may include, silicon (Si), strained Si, a silicon alloy, silicon carbide (SiC), silicon germanium (SiGe), silicon germanium carbide (SiGeC), germanium, a germanium alloy, gallium arsenide (GaAs), indium arsenide (InAs), one of III-V group semiconductor compounds, one of II-VI group semiconductor compounds, and stacks thereof. In addition, the substrate 450 may be an organic plastic substrate, rather than a semiconductor substrate.

The substrate defect inspecting apparatus 4 may be configured to inspect defects existing on bottom surfaces of contact holes formed in a stacked structure provided on the substrate 450.

The detector 480 detects the IR_beam reflected from the substrate 450 and having through the beam splitter 430. A state of the substrate 450 or states of the bottom surfaces of the contact holes may be identified using the IR_beam detected by the detector 480. For example, when the information concerning a defect existing in the substrate 450 is known and the information concerning defects existing on the bottom surfaces of the contact holes is known, it is possible to obtain information concerning defects generated during a contact hole forming process.

The defects existing on the bottom surfaces of the contact holes may be overgrowth defects or missing defects. When the overgrowth defects or missing defects are produced on the bottom surfaces of the contact holes, the IR_beam having different amounts of light is reflected, and the intensity of the IR_beam detected by the detector 480 may vary.

The image processor 490 converts an analog signal received from the detector 480 into a digital image. The image processor 490 generates the digital image using the information concerning the intensity of the IR_beam detected by the detector 480. That is to say, a digitized defect image is overlapped with the image of the substrate 450, thereby providing the digital image to allow a user to easily identify defects existing in the substrate 450.

The defect analyzer 500 generates a fourth defect image and a fifth defect image based on the digital image provided from the image processor 490, compares the fourth defect image with the fifth defect image, and analyzes defects existing on the bottom surfaces of the contact holes.

According to at least one example embodiment, the defect analyzer 500 may be configured to analyze the defects existing on the bottom surfaces of the contact holes, which are generated in the contact hole forming process, using a digital image i4 concerning the defects existing in the substrate 450 and a digital image i5 concerning the defects existing on the bottom surfaces of the contact holes.

When the digital image i4 concerning the defects existing in the substrate 50 is subtracted from the digital image i5 concerning the defects existing on the bottom surfaces of the contact holes, only a digital image i6 concerning defects generated in the contact hole forming process may be obtained, thereby easily identifying the defects existing on the bottom surfaces of the contact holes.

The defect analyzer 500 may be configured to perform contact hole inspection based on desired, or alternatively predetermined coordinate information on the substrate 450. That is to say, coordinates of the substrate 450 may be generated and contact holes may be formed at locations corresponding to the coordinates. The locations where contact holes are formed may be identified using the desired, or alternatively predetermined coordinate information by repeating the contact hole forming processes, and the defects existing on the bottom surfaces of the contact holes can be inspected by emitting IR_beam to the locations in the above-described manner.

Figure 16:
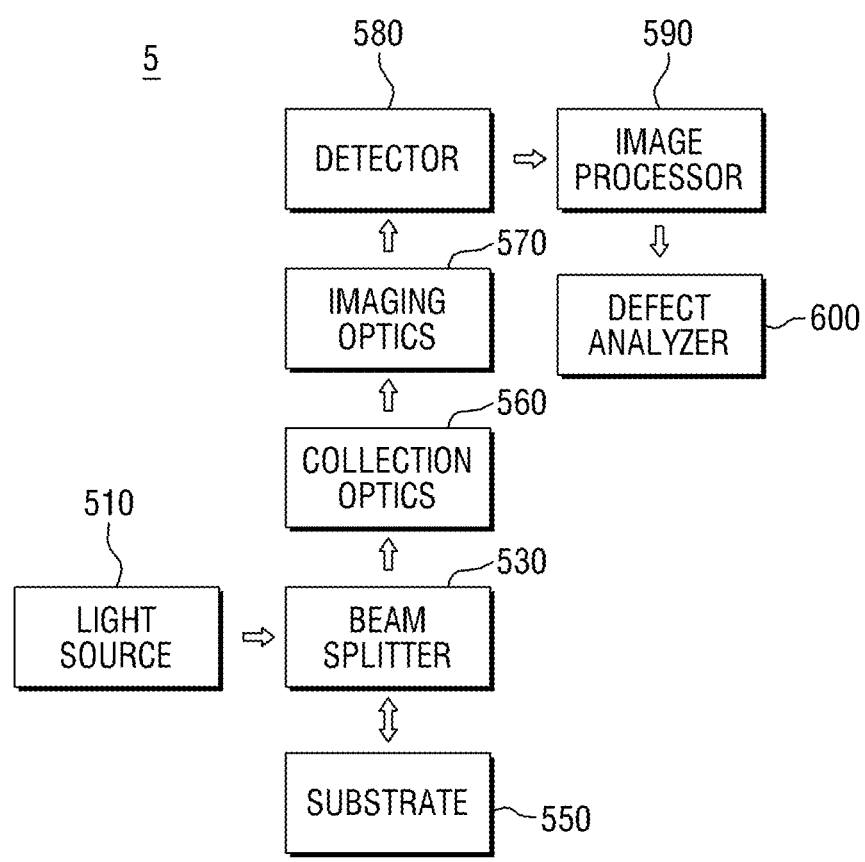
FIG. 16 is a block diagram of a substrate defect inspecting apparatus according to at least one example embodiment.

FIG. 16 is a block diagram of a substrate defect inspecting apparatus according to at least one example embodiment. For brevity, substantially the same portions of the substrate defect inspecting apparatus according to the current example embodiment as those of the substrate defect inspecting apparatus according to the above example embodiment will not be repeated.

Referring to FIG. 16, the substrate defect inspecting apparatus 5 according to at least one example embodiment includes a light source 510, a beam splitter 530, a substrate 550, a collecting optics 560, an imaging optics 570, a detector 580, an image processor 590, and a defect analyzer 600.

The light source 510 emits an IR_beam to the beam splitter 530. Here, the light source 510 may emit the IR_beam, which has a wavelength ranging from about 600 nm to about 900 nm.

The light source 510 emitting the IR_beam may be, for example, a laser diode (LD) or a light emitting diode (LED), but example embodiments are not limited thereto. The output power of the IR_beam emitted from the light source 510 may be adjusted.

The beam splitter 530 is configured to receive and reflect the IR_beam received from the light source 510 or to allow the IR_beam reflected from the substrate 550 to pass therethrough.

The substrate 550 may be a semiconductor substrate. The substrate 550 may include, silicon (Si), strained Si, a silicon alloy, silicon carbide (SiC), silicon germanium (SiGe), silicon germanium carbide (SiGeC), germanium, a germanium alloy, gallium arsenide (GaAs), indium arsenide (InAs), one of III-V group semiconductor compounds, one of II-VI group semiconductor compounds, and stacks thereof. In addition, the substrate 550 may be an organic plastic substrate, rather than a semiconductor substrate.

The substrate defect inspecting apparatus 5 may be configured to inspect defects existing on bottom surfaces of contact holes formed in a stacked structure provided on the substrate 550.

The collecting optics 560 focuses the IR_beam reflected from the substrate 550 and having passed through the beam splitter 530. That is to say, the IR_beam reflected from the substrate 550 passes through the beam splitter 530 and the IR_beam having passed through the beam splitter 530 is focused by the collecting optics 560, thereby obtaining various pieces of information.

If the IR_beam is focused by the collecting optics 560, the intensity of light reaching the detector 580 may be increased, thereby easily obtaining information on the IR_beam reflected from the substrate 550 or reflected from bottom surfaces of contact holes.

The imaging optics 570 transforms the state of the IR_beam having passed through the collecting optics 560 or changes a magnification of the collecting optics 560. That is to say, the imaging optics 570 may also be an aperture, a polarizer or a homogenizer.

When the imaging optics 570 includes various types of apertures, the IR_beam having passed through the collecting optics 560 may be transformed to have various shapes according to the aperture type. Since the intensity of the IR_beam reaching the detector 580 may vary, it may be advantageous to use an aperture having optimal conditions.

Alternatively, the imaging optics 570 may include various types of polarizers. When the imaging optics 570 includes various types of polarizers, the direction of polarization of the IR_beam having passed through the collecting optics 560 may be adjustable. Since the intensity of the IR_beam reaching the detector 580 may vary according to the direction of polarization, it may be advantageous to adjust the direction of polarization so as to provide the optimal conditions.

Further, the imaging optics 570 may include various types of homogenizers. When the imaging optics 570 includes various types of homogenizer, the intensity of the IR_beam reaching the detector 580 may vary. Therefore, it may be advantageous to use a homogenizer providing the optimal conditions.

The detector 580 detects the IR_beam reflected from the substrate 550 and having passed through the beam splitter 530, the collecting optics 560 and the imaging optics 570. A state of the substrate 550 or states of the bottom surfaces of the contact holes may be identified using the IR_beam detected by the detector 580. For example, when the information concerning a defect existing in the substrate 550 is known and the information concerning defects existing on the bottom surfaces of the contact holes is known, it is possible to obtain information concerning defects generated during a contact hole forming process.

The defects existing on the bottom surfaces of the contact holes may be overgrowth defects or missing defects. When the overgrowth defects or missing defects are produced on the bottom surfaces of the contact holes, the IR_beam having different amounts of light is reflected, and the intensity of the IR_beam detected by the detector 580 may vary.

The image processor 590 converts an analog signal received from the detector 580 into a digital image. The image processor 590 generates the digital image using the information concerning the intensity of the IR_beam detected by the detector 580. That is to say, a digitized defect image is overlapped with the image of the substrate 550, thereby providing the digital image to allow a user to easily identify defects existing in the substrate 550.

The defect analyzer 600 generates a seventh defect image and an eighth defect image based on the digital image provided from the image processor 590, compares the seventh defect image with the eighth defect image, and analyzes defects existing on the bottom surfaces of the contact holes.

According to at least one example embodiment, the defect analyzer 600 may analyze the defects existing on the bottom surfaces of the contact holes, which are generated in the contact hole forming process, using a digital image i7 concerning the defects existing in the substrate 550 and a digital image i8 concerning the defects existing on the bottom surfaces of the contact holes.

If the digital image i7 is subtracted from the digital image i8, only a digital image i9 concerning defects generated during the contact hole forming process may be obtained, thereby easily identifying the defects existing on the bottom surfaces of the contact holes.

The defect analyzer 600 may perform contact hole inspection based on desired, or alternatively predetermined coordinate information on the substrate 550. That is to say, coordinates of the substrate 550 may be generated and contact holes may be formed at locations corresponding to the coordinates. The locations at which contact holes are formed may be identified using the desired, or alternatively predetermined coordinate information by repeating the contact hole forming processes, and the defects existing on the bottom surfaces of the contact holes can be inspected by emitting IR_beam to the locations in the above-described manner.

Hereinafter, a substrate defect inspecting method according to at least one example embodiment will be described.

Figure 17:
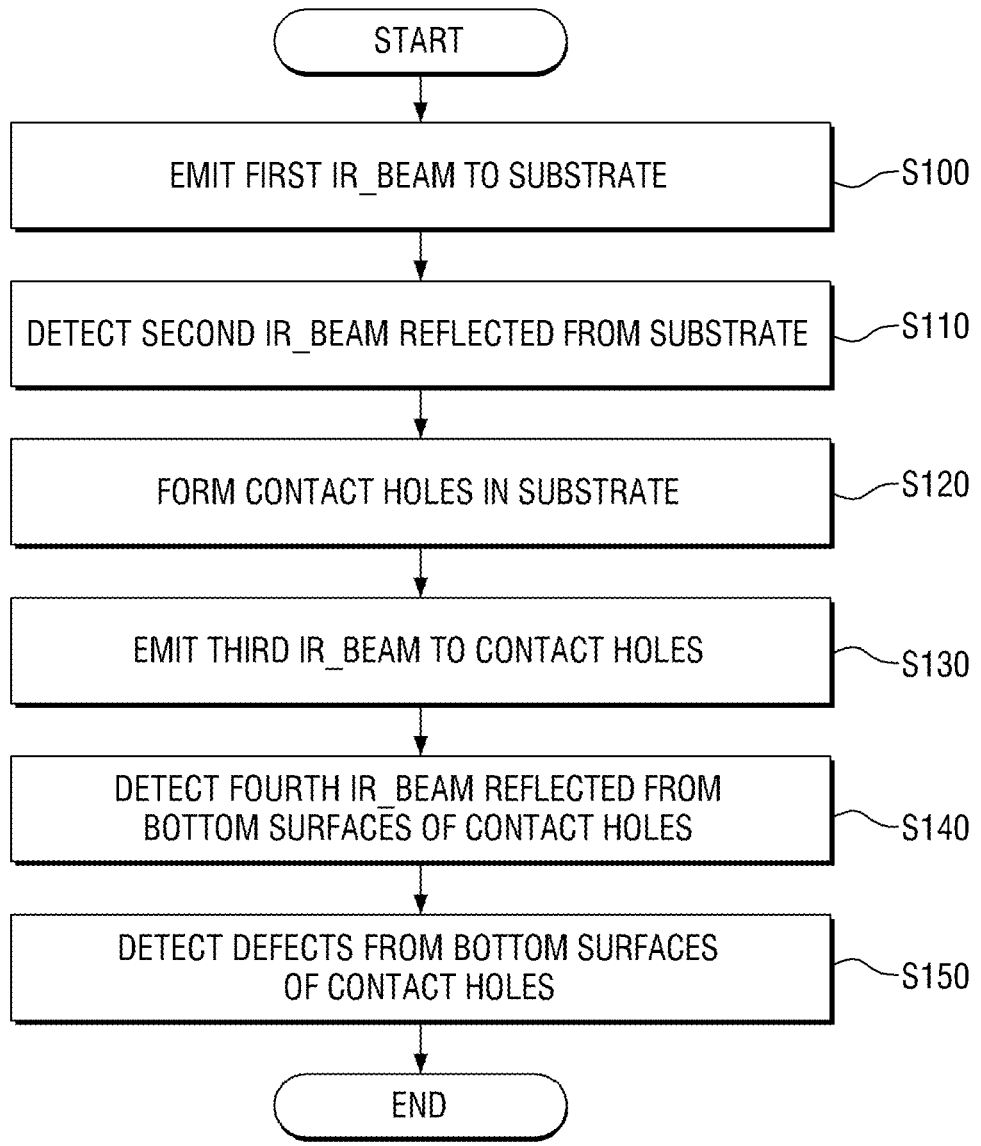
FIG. 17 is a flowchart sequentially illustrating a substrate defect inspecting method according to at least one example embodiment.

FIG. 17 is a flowchart sequentially illustrating a substrate defect inspecting method according to at least one example embodiment.

Referring to FIG. 17, the substrate defect inspecting method according to at least one example embodiment includes emitting a first infrared beam IR_1 toward a substrate (S100). Here, the first infrared beam IR_1 emitted from a light source may reach the substrate through a beam shaper, a beam splitter, a focusing optics, and so on, but example embodiments are not limited thereto. That is to say, the first infrared beam IR_1 may not pass through at least one of the beam shaper, the beam splitter and the focusing optics.

For example, the first infrared beam IR_1 may have a wavelength ranging from about 600 nm to about 900 nm. The light source emitting the first infrared beam IR_1 may be, for example, a laser diode LD or a light emitting diode (LED), but example embodiments are not limited thereto.

Next, a second infrared beam IR_2 reflected from the substrate is detected (S110). Here, the second infrared beam IR_2 reflected from the substrate may reach a detector through a focusing optics, a beam splitter, a collecting optics, an imaging optics and so on, but example embodiments are not limited thereto. That is to say, the second infrared beam IR_2 may not pass through at least one of the focusing optics, the beam splitter, the collecting optics and the imaging optics.

Similarly to the first infrared beam IR_1, the second infrared beam IR_2 may have a wavelength ranging from about 600 nm to about 900 nm, because the second infrared beam IR_2 corresponds to the first infrared beam IR_1 reflected from the substrate.

Next, contact holes are formed in the substrate (S120). The contact holes may be formed for the purpose of electrically connecting top and bottom portions of the substrate having a stacked structure formed thereon. Before the contact holes are filled with conductive materials, in order to avoid contact failures, it may be advantageous to inspect whether defects are generated in the contact holes. In addition, the substrate defect inspecting method according to at least one example embodiment may be utilized to inspect whether overgrowth defects or missing defects are generated on bottom surfaces of the contact holes.

After the forming of the contact holes in the substrate (S120), a third infrared beam IR_3 is emitted to the contact holes (S130).

The third infrared beam IR_3 may also have a wavelength ranging from about 600 nm to about 900 nm. The light source emitting the third infrared beam IR_3 may be, for example, a laser diode (LD) or a light emitting diode (LED), but example embodiments are not limited thereto.

When the wavelength of the third infrared beam IR_3 ranges from about 600 nm to about 900 nm, the third infrared beam IR_3 may penetrate as deep as the bottom surfaces of the contact holes. Therefore, in order to increase the efficiency of inspecting defects generated on the bottom surfaces of the contact holes, the wavelength of the third infrared beam IR_3 is preferably in a range of about 600 nm to about 900 nm.

Next, a fourth infrared beam IR_4 reflected from the bottom surfaces of the contact holes is detected (S140).

Like the third infrared beam IR_3, the fourth infrared beam IR_4 may have a wavelength ranging from about 600 nm to about 900 nm, because the fourth infrared beam IR_4 corresponds to the third infrared beam IR_3 reflected from the substrate.

Next, defects existing on the bottom surfaces of the contact holes are detected using the second infrared beam IR_2 and the fourth infrared beam IR_4 (S150). According to at least one example embodiment, a state of the defect existing in the substrate is inspected by extracting a light signal 51 from the second infrared beam IR_2, and states of the defects existing on the bottom surfaces of the contact holes are inspected by extracting a light signal S2 from the fourth infrared beam IR_4. Here, the fourth infrared beam IR_4 is the beam reflected from the substrate on which defect inspection has already been performed after the contact holes are formed in the substrate. Thus, the light signal S2 extracted from the fourth infrared beam IR_4 includes information concerning both the defects existing on the bottom surfaces of the contact holes and information concerning a defect existing in the substrate prior to the contact hole forming process. Accordingly, it is possible to inspect the defects existing on the bottom surfaces of the contact holes, generated during the contact hole forming process, using SDA.

In particular, defect inspection may be performed based on desired, or alternatively predetermined coordinate information of the substrate. Locations at which contact holes are formed may be identified using the desired, or alternatively predetermined coordinate information by repeating the contact hole forming processes, and the defects existing on the bottom surfaces of the contact holes can be inspected by emitting first and third infrared beams IR_1 and IR_3 to the locations in the above-described manner.

Figure 18:
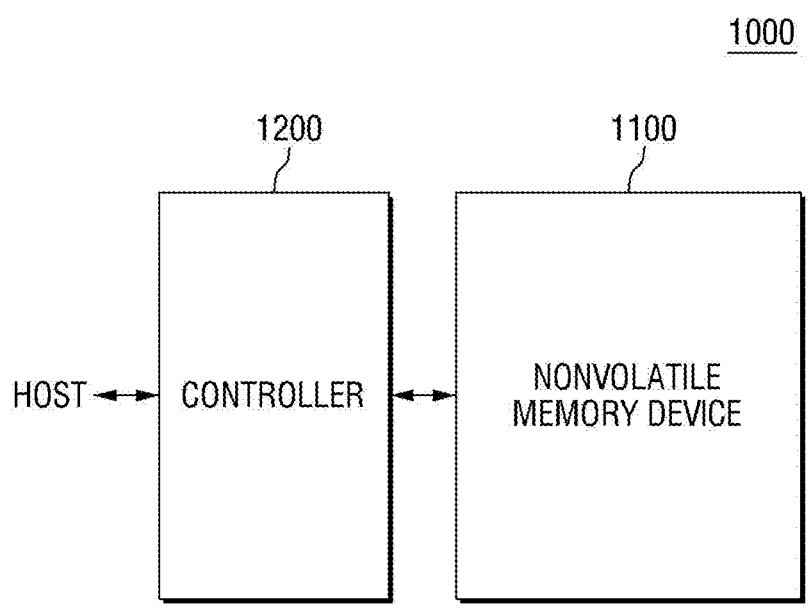
FIG. 18 is a block diagram illustrating a memory system including a nonvolatile memory device fabricated using a substrate defect inspecting apparatus according to example embodiments.

FIG. 18 is a block diagram illustrating a memory system including a nonvolatile memory device fabricated using a substrate defect inspecting apparatus according to example embodiments.

Referring to FIG. 18, the memory system 1000 includes a nonvolatile memory device 1100 and a controller 1200.

The nonvolatile memory device 1100 may be provided as, for example, a vertical NAND flash memory.

The controller 1200 is connected to a host and the nonvolatile memory device 1100.

The controller 1200 may access the nonvolatile memory device 1100 at a request from the host. For example, the controller 1200 may control read, write, erase, and background operations of the nonvolatile memory device 1100.

The controller 1200 provides interfacing between the nonvolatile memory device 1100 and the host. The controller 1200 may drive firmware for controlling the nonvolatile memory device 1100.

As an example, the controller 1200 may further include well-known components, such as a random access memory (RAM), a processing unit, a host interface, a memory interface, or the like.

The RAM may be used as at least one of a working memory of the processing unit, a cache memory between the nonvolatile memory device 1100 and the host, and a buffer memory between the nonvolatile memory device 1100 and the host.

The processing unit controls the overall operation of the controller 1200.

The host interface may include a protocol to exchange data between the host and the controller 1200. For example, the controller 1200 may be configured to communicate with an external device (host) through one of various interface protocols such as universal serial bus (USB), multimedia card (MMC), peripheral component interconnection (PCI) protocol, PCI-express (PCI-E) protocol, advanced technology electronics (ATA) protocol, serial-ATA protocol, parallel-ATA protocol, small computer small interface (SCSI) protocol, enhanced small disk interface (ESDI) protocol, and integrated drive electronics (IDE) protocol.

The memory interface may interface with the nonvolatile memory device 1100. Here, the memory interface may include, for example, a NAND interface or a NOR interface.

The memory system 1000 may further include an error correction block. The error correction block may be configured to detect and correct an error of the data stored in the memory system 1100 using an error correction code (ECC). As an example, the error correction block may be provided as a component of the controller 1200.

Alternatively, the error correction block may also be provided as a component of the nonvolatile memory device 1100.

The controller 1200 and the nonvolatile memory device 1100 may be integrated into one semiconductor device. As an example, the controller 1200 and the nonvolatile memory device 1100 may be integrated into one semiconductor device to form a memory card.

For example, the controller 1200 and the nonvolatile memory device 1100 may be integrated into one semiconductor device to form a memory card, such as a PC card (originally PCMCIA or PCMCIA card), a Compact Flash (CF) card, a Smart Media (SM) Card, a memory stick, a multimedia card (MMC, RS-MMC, MMCmicro), a Secure Digital card (SD, miniSD, microSD), a Universal Flash storage (UFS), or the like.

The controller 1200 and the nonvolatile memory device 1100 may be integrated into one semiconductor device to form a solid state disk/drive (SSD). The SSD includes a storage device configured to store data in a semiconductor memory. When the memory system 1000 is used as the SSD, the operating speed of the host connected to the memory system 1000 is remarkably improved.

In example embodiments, the memory system 1000 may be implemented as a computer, an ultra-mobile personal computer (UMPC), a work station, a net-book, a personal digital assistant (PDA), a portable computer, a web tablet, a wireless phone, a mobile phone, a smart phone, an e-book, a portable multimedia player (PMP), a potable game console, a navigation device, a black box, a digital camera, a 3-dimensional (3D) television, a digital audio recorder, a digital audio player, a digital picture recorder, a digital picture player, a digital video recorder, a digital video player, or a device capable of transmitting/receiving information in wireless environments, one of various electronic devices constituting a home network, one of various electronic devices constituting a computer network, one of various electronic devices constituting a telematics network, RFID devices, or embedded computing systems.

As an example, the nonvolatile memory device 1100 or the memory system 1000 may be mounted in various types of packages. Examples of the packages of the nonvolatile memory device 1100 or the memory system 1000 may include Package on Package (PoP), Ball Grid Arrays (BGAs), Chip Scale Packages (CSPs), Plastic Leaded Chip Carrier (PLCC), Plastic Dual In-line Package (PDIP), Die in Waffle Pack, Die in Wafer Form, Chip On Substrate (COB), Ceramic Dual In-line Package (CERDIP), Plastic Metric Quad Flat Pack (MQFP), Thin Quad Flat Pack (TQFP), Small Outline Integrated Circuit (SOIC), Shrink Small Outline Package (SSOP), Thin Small Outline Package (TSOP), Thin Quad Flatpack (TQFP), System In Package (SIP), Multi Chip Package (MCP), Wafer-level Fabricated Package (WFP), and Wafer-Level Processed Stack Package (WSP).

Figure 19:
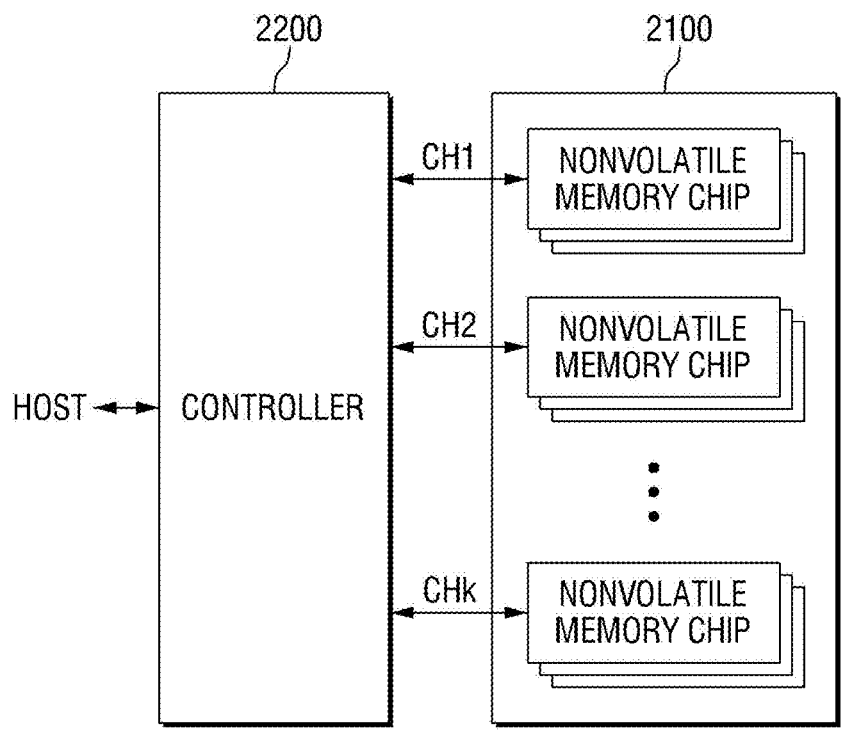
FIG. 19 is a block diagram for explaining an application example of the memory system shown in FIG. 18.

FIG. 19 is a block diagram for explaining an application example of the memory system shown in FIG. 18.

Referring to FIG. 19, the memory system 2000 includes a nonvolatile memory device 2100 and a memory controller 2200.

The nonvolatile memory device 2100 may include a plurality of memory chips. The plurality of memory chips may be divided into a plurality of groups. The respective groups of the plurality of memory chips may interface with the memory controller 2200 through a common channel. For example, the respective groups of the plurality of memory chips may interface with the memory controller 2200 through first to lth channels CH1 to CH1.

While the plurality of memory chips connected to one channel are exemplified in FIG. 19, the memory system 2000 may be modified such that one memory chip is connected to one channel.

Figure 20:
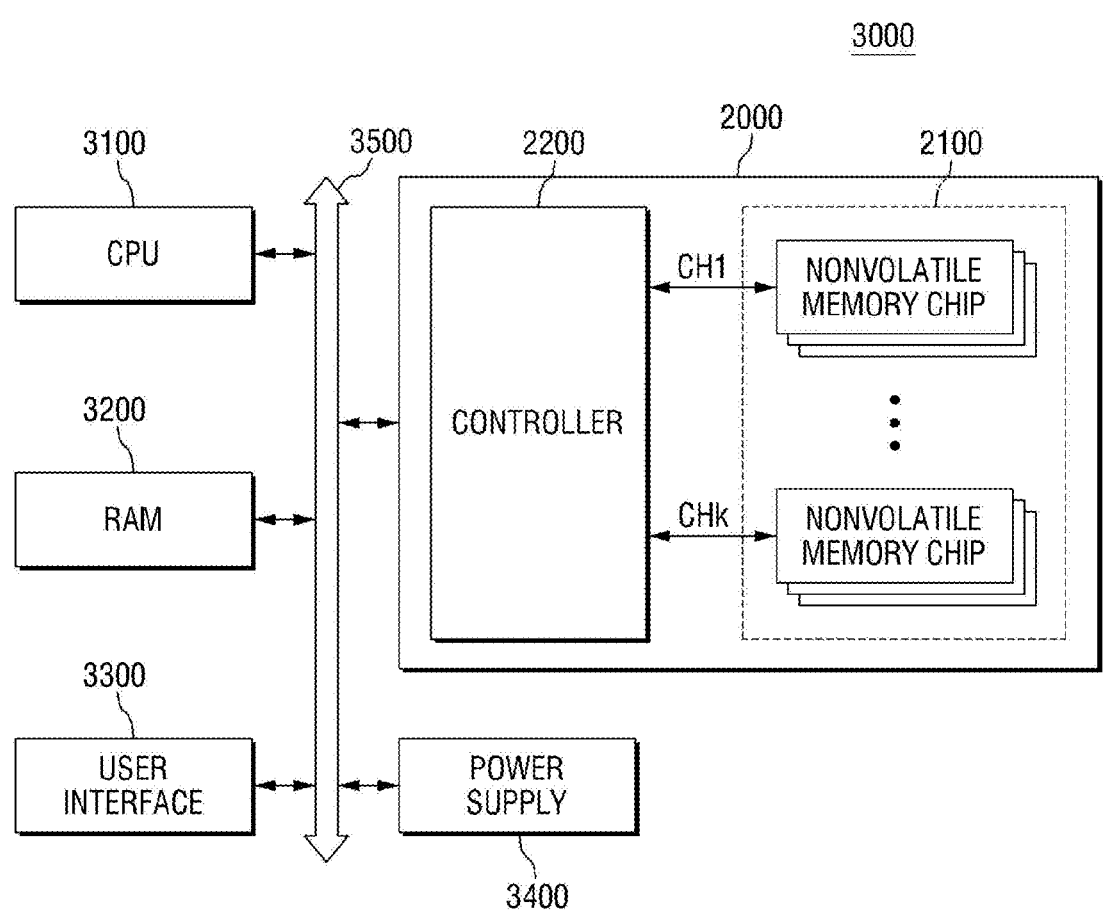
FIG. 20 is a block diagram illustrating a computing system including the memory system shown in FIG. 18 or 19.

FIG. 20 is a block diagram illustrating a computing system including the memory system shown in FIG. 18 or 19.

Referring to FIG. 20, the computing system 3000 includes a central processing unit (CPU) 3100, a random access memory (RAM) 3200, a user interface 3300, a power supply 3400, and a memory system 2000.

The memory system 2000 may be electrically connected to the CPU 3100, the RAM 3200, the user interface 3300 and the power supply 3400 through a system bus 3500. The data supplied through the user interface 3300 or processed by the CPU 3100 may be stored in the memory system 2000.

In FIG. 20, the nonvolatile memories 2100 are connected to a system bus 3500 through the controller 2200. However, unlike in FIG. 20, the nonvolatile memories 2100 may be configured to be directly connected to the system bus 3500.

In FIG. 20, the memory system 2000 shown in FIG. 19 is provided in the computing system. However, the memory system 2000 may be replaced with the memory system 1000 shown in FIG. 18.

As an example, the computing system 3000 may be configured to both of the memory systems 1000 and 2000 shown in FIGS. 18 and 19.

While at least one example embodiment has been particularly shown and described with reference to exemplary embodiments thereof, it will be understood by those of ordinary skill in the art that various changes in form and details may be made therein without departing from the spirit and scope of the example embodiments as defined by the following claims. It is therefore desired that the example embodiments be considered in all respects as illustrative and not restrictive, reference being made to the appended claims rather than the foregoing description to indicate the scope of the example embodiments.

What is claimed is:

1. A substrate defect inspecting apparatus comprising:
a substrate;
a light source configured to emit an infrared beam on the substrate;
a detector configured to detect the infrared beam reflected from the substrate; and
a defect analyzer configured to receive first information and second information from the detector and to analyze defects in the substrate,
wherein the defect analyzer is configured to receive the first information before a manufacturing process and the second information after the manufacturing process, and
wherein the first and second information are based on same desired coordinate information of the substrate.

2. The substrate defect inspecting apparatus of claim 1, wherein the infrared beam has a wavelength ranging from about 600 nm to about 900 nm.

3. The substrate defect inspecting apparatus of claim 1, wherein the defects are in a contact hole of the substrate.

4. The substrate defect inspecting apparatus of claim 3, wherein the defects are at least one of overgrowth defects and missing defects.

5. The substrate defect inspecting apparatus of claim 3, wherein the defect analyzer is configured to inspect the contact holes based on desired coordinate information of the substrate.

6. A substrate defect inspecting apparatus comprising:
a substrate;
a light source configured to emit an infrared beam on the substrate;
a detector configured to detect the infrared beam reflected from the substrate;
an image processor configured to convert an analog signal received from the detector into a digital image; and
a defect analyzer configured to create first and second defect images based on the digital image, and configured to detect defects in the substrate based on the first and second defect images,
wherein the first and second defect images are based on same desired coordinate information of the substrate; and
wherein the defect analyzer is configured to create the first defect images before a manufacturing process and to create the second defect images after the manufacturing process.

7. The substrate defect inspecting apparatus of claim 6, further comprising:
a beam shaper configured to receive the infrared beam emitted from the light source and to transform a state of the infrared beam.

8. The substrate defect inspecting apparatus of claim 7, wherein the beam shaper is an aperture, a polarizer or a homogenizer.

9. The substrate defect inspecting apparatus of claim 7, further comprising:
a beam splitter configured to receive and to reflect the infrared beam having passed through the beam shaper and to allow the infrared beam reflected from the substrate to pass therethrough.

10. The substrate defect inspecting apparatus of claim 9, further comprising:
a collecting optical system configured to focus the infrared beam having passed through the beam splitter.

11. The substrate defect inspecting apparatus of claim 10, further comprising:
an imaging optical system configured to at least one of transform a state of the infrared beam having passed through the collecting optical system and to vary a magnification of the collecting optical system.

12. A substrate defect inspecting apparatus comprising:
a light source configured to emit light having a wavelength ranging from about 600 nm to about 900 nm;
a contact hole bottom surface configured to receive and reflect the light; and
a defect detecting architecture configured to detect the light reflected from the contact hole bottom surface and configured to detect first and second defects in the contact hole bottom surface based on the detected reflected light,
wherein the defect detecting architecture is configured to detect the first defects before a manufacturing process and the second defects after the manufacturing process.

13. The substrate defect inspecting apparatus of claim 12, wherein the first and second defects are at least one of overgrowth defects and missing defects generated on the contact hole bottom surface by the manufacturing process.

14. A defect analyzing apparatus, comprising:
a substrate;
a light source configured to emit a radiation beam on the substrate;
a detector configured to detect a first reflected infrared beam from the substrate and a second reflected infrared beam from the substrate, the first reflected infrared beam corresponding to a first state of the substrate and the second reflected infrared beam corresponding to a second state of the substrate; and
a defect analyzer configured to analyze defects in the substrate based on the detected first reflected infrared beam and the detected second reflected infrared beam;
wherein the first state is a state of the substrate before a manufacturing process and the second state is the state of the substrate after the manufacturing process.

15. The defect analyzing apparatus of claim 14, wherein
the first state corresponds to the substrate having no contact holes formed therein, and
the second state corresponds to the substrate having contact holes formed therein.

16. The defect analyzing apparatus of claim 14, wherein a wavelength of the radiation beam is in a range of about 600 nm to about 900 nm.

17. The defect analyzing apparatus of claim 14, wherein the analyzed defects comprise contact hole defects.

* * * * *